United States Patent
Bissinger

[11] Patent Number: 6,147,136
[45] Date of Patent: Nov. 14, 2000

[54] DENTAL COMPOSITIONS BASED ON ROMP OLIGOMERS AND POLYMERS

[75] Inventor: Peter Bissinger, Mering, Germany

[73] Assignee: ESPE Dental AG, Beedfeld, Germany

[21] Appl. No.: 09/162,454

[22] Filed: Sep. 29, 1998

[30] Foreign Application Priority Data

Sep. 29, 1997 [DE] Germany .................... 197 42 980

[51] Int. Cl.$^7$ .................................. A61K 6/083
[52] U.S. Cl. .................. 523/116; 523/115; 523/118; 523/406; 523/410; 523/467; 524/549
[58] Field of Search .................... 523/115, 116, 523/118, 406, 410, 467; 524/549

[56] References Cited

U.S. PATENT DOCUMENTS

| | | | |
|---|---|---|---|
| 4,722,948 | 2/1988 | Sanderson | 523/115 |
| 4,855,234 | 8/1989 | Hendrickson | 435/181 |
| 4,872,936 | 10/1989 | Engelbrecht | 523/118 |
| 5,019,379 | 5/1991 | Domb et al. | 523/116 |
| 5,539,060 | 7/1996 | Tsunogae et al. | |

FOREIGN PATENT DOCUMENTS

| | | | |
|---|---|---|---|
| 2199567 | 3/1997 | Canada | 523/116 |
| 0792881 | 9/1997 | European Pat. Off. | |
| 19608313 | 8/1997 | Germany | |
| 19616183 | 9/1997 | Germany | |

OTHER PUBLICATIONS

Patent Abstract of Japan C–293 Mar. 31, 1992 vol. 16/No. 126.

*Primary Examiner*—Andrew E. C. Merriam
*Attorney, Agent, or Firm*—Birch, Stewart, Kolasch & Birch LLP

[57] ABSTRACT

The invention relates to dental compositions containing (a) 5 to 70 wt. %, relative to (a)+(b)+(d), of oligomers and/or polymers,
(b) 0 to 95 wt. %, relative to (a)+(b)+(d), of fillers,
(c) 0.1 to 3 wt. %, relative to (a), of at least one initiator or one initiator system,
(d) 0 to 95 wt. %, relative to (a)+(b)+(d), of the usual adjuncts, including pigments, radiopaque additives and/or thixotropy auxiliaries, characterized in that 5 to 100 wt. % of component (a) comprises oligomers or polymers with the general formula

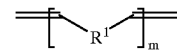

or

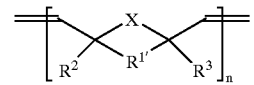

The dental compositions are suitable for producing filling materials, fixing cements, inlays, onlays, veneers, temporary crown and bridge materials, dentistry and impression materials. In compositions with radical curing, slight volume shrinkage occurs during curing, whereas in cement compositions, better mechanical properties are obtained.

23 Claims, No Drawings

DENTAL COMPOSITIONS BASED ON ROMP OLIGOMERS AND POLYMERS

The present invention relates to dental compositions containing oligomers or polymers obtained by ring-opening metathesis polymerization.

Ethylenically-unsaturated monomers, preferably methacrylate and acrylate monomers, have mainly been used until now in polymerizable dental compositions. 2,2-Bis(4, 1-phenyleneoxy (2-hydroxy-3,1-propanediyl)-methacrylate)-propylidene (bis-GMA), described by Bowen (U.S. Pat. No. 3,066,112) is used particularly often. Mixtures of this methacrylate with triethyleneglycol dimethacrylate (TEGDMA) still serve as the standard recipe for dental plastic direct-filling materials. Curing of these compositions is based on a radical polymerization reaction which is initiated by appropriately activated radical-forming initiators. The adverse polymerization shrinkage that occurs during polymerization is problematic. For example, during application as filling material, this can lead to the formation of discoloration at the edge of the tooth cavity or even to the development of marginal gaps with the associated risk of secondary caries.

As well as these radical-polymerizing systems, two-component systems, resulting from a cement reaction between a reactive filler and a liquid that reacts with this filler, are also used as dental filling and fixing materials. Examples of this are the phosphate, silicate, carboxylate (DE-B-1 617 688) and glass-ionomer cements (DE-A-2 101 889). A general survey of this field is given for example in A. D. Wilson: Chemical Society Reviews (1978), 7, (2), 265–296 or in D. Welker, A. Rzanny, R. Göbel; Dental Magazin (1997), 2, 64–76. Compared with the radical-polymerizing dental compositions, these cement materials have the great drawback that their mechanical properties such as compressive strength and bending strength are markedly inferior. The reason for this is, in the case of the glass-ionomer cements, among other things a very high flexibility of the polycarboxylic acid of the liquid.

The task of the present invention is to elaborate dental materials containing oligomers and polymers, which lead in the case of radical-polymerizing systems to little volumetric shrinkage and in the case of cement systems to better mechanical properties.

This task is fulfilled by the provision of compositions which contain:

(a) 5 to 70 wt. %, preferably 10 to 60 wt. %, based on (a)+(b)+(d), of monomers, oligomers and/or polymers, (b) 0 to 95 wt. %, preferably 40 to 85 wt. %, based on (a)+(b)+(d), of fillers, (c) 0.1 to 3 wt. %, preferably 3 wt. %, especially to 2.0 wt. %, based on (a), of at least one initiator or one initiator system, and (d) 30 wt %, especially to 95 wt. %, preferably 5 to 30 wt. %, based on (a)+(b)+(d), of the usual adjuncts, including pigments, radiopaque additives and/or thixotropy auxiliaries, characterized in that 5 to 100 wt. % of component (a) are oligomers or polymers with the general formula

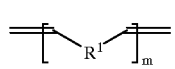

(I)

or

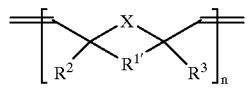

(II)

in which:

X denotes $CH_2$, NH, O or S, m has a value from 10 to 20 000, n has a value from 10 to 20 000, $R^1$ denotes $-CHR^4-CHR^5-$, $-CR^4=CR^5-$

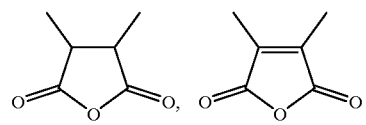

$C_2-C_{10}$-alkylene, $C_2-C_{10}$-alkenylene, $C_2-C_{10}$-epoxyalkylene, or $C_6-C_{15}$-o-arylene which can be substituted by alkyl, OH, $NH_2$, $C(O)OR^6$, $C(O)NHR^6$, $PO_3H$, $SO_3H$, Cl, Br or F, $R^{1'}$ denotes $-CHR^4-CHR^5-$, $CR^4=CR^5-$

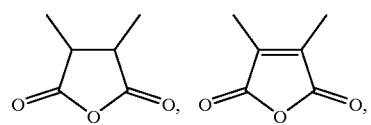

$R^2$, $R^3$, $R^4$, $R^5$ denote H, $C_1-C_{15}$-alkyl, $C(O)OR^6$, $C(O)NHR^6$, $PO_3H$, $SO_3H$, OH and $R^6$ denotes H or a linear, branched or cyclic $C_1-C_{30}$-alkyl or aryl residue, which can contain 0–10 O or N atoms and 0 to 5 carbonyl groups and is saturated or unsaturated, with the proviso that these compounds contain groups which lead to curing of the compositions by radical or cationic polymerization or by a cement reaction.

Oligomers or polymers of general formulae I and II can be obtained by ring-opening metathesis polymerization (ROMP). Ring-opening metathesis polymerization is known from the literature and has also been used industrially for some years (Comprehensive Polymer Sci.; 4, 109–142). Uses of these oligomers or polymers obtained by ROMP for dental applications are not known.

Within the scope of this invention it was found, surprisingly, that compounds with the general formulae (I) and (II) are very suitable for dental purposes and give compositions with special properties. In the case of radical-polymerizing systems there is less volume shrinkage, and better mechanical properties are obtained with cement systems. This applies whether the compounds of formulae (I) and (II) are contained individually or as a mixture in the dental compositions.

Compounds with the general formulae (I) and (II), which in the dental compositions disclosed here lead to curing by radical polymerization, are those that are at least simply ethylenically unsaturated. Compounds containing acrylate or methacrylate groups are preferred.

Compound (III) with m=1000–3000 is especially preferred:

(III)

(IV)

(V)

(VI)

(VII)

(VIII)

These ethylenically unsaturated oligomers or polymers can be used in the disclosed dental compositions either alone or in combination with other ethylenically unsaturated monomers. Ethylenically unsaturated co-monomers whose use is preferred are acrylates or methacrylates. Especially preferred ethylenically unsaturated co-monomers are bis-GMA, TEGDMA, bis-(hydroxymethyl)tricyclo(5.2.1.0$^{2,6}$)-decane-diacrylate and 2,2-bis(4,1-phenyleneoxy(3,1-propanediyl)-methacrylate)-propylidene.

Other preferred compounds are shown in formulae (IV)–(VIII) (with m=1000–3000):

Compounds (III)–(VII) are synthesized in each case by ROMP of corresponding norbornene derivatives, which are in turn obtained by Diels-Alder reaction. A general description of these reaction sequences is given, for example, in "Comprehensive organometallic Chemistry II: a review of the literature 1982–1994", Elsevier 1995, pages 1209–1232. Compound (VIII) can be produced according to the information from A. Demonceau et al. in Macromolecules (1997), 30, pages 3127 to 3136.

Radical-forming catalysts according to constituent (c) for curing these ethylenically unsaturated monomers, oligomers and polymers can be substances that can be activated by UV or visible light, for example benzoinalkylether, benzyl ketals, acylphosphine oxides or aliphatic and aromatic 1,2-diketone compounds, e.g. camphor quinone, it being possible for the photochemical polymerization to be accelerated in a known way by adding activators, such as tertiary amines or organic phosphites.

Suitable initiator systems for initiating radical polymerization by a redox mechanism are for example the systems peroxide/amine or peroxide/barbituric acid derivatives and the like. When using initiator systems of this kind it is advisable to prepare an initiator (e.g. peroxide) and a catalyst component (e.g. amine) separately. The two components are then mixed together homogeneously shortly before use.

Compounds with the general formulae (I) and (II), which in the dental compositions disclosed here are cured by cationic polymerization, are preferably those that are epoxy-functionalized. Especially preferred compounds of this type are shown in formulae (IX) to (XIV) (with m=1000 to 3000):

(IX)

-continued

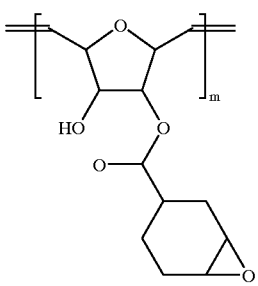

(X)

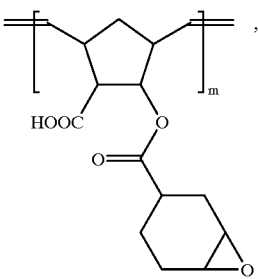

(XI)

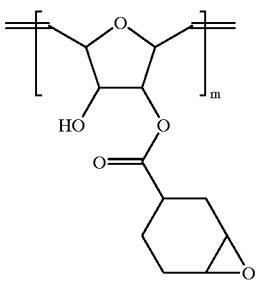

(XII)

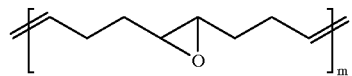

(XIII)

Compounds (IX) to (XII) can once again be synthesized from the corresponding precursors as described in "Comprehensive organometallic Chemistry II: a review of the literature 1982–1994", Elsevier 1995, pages 1209–1232. Compound (XIII) can be produced according to the information from A. Demonceau et al. in Macromolecules (1997), 30, pages 3127 to 3136.

The cationically polymerizable compounds according to formulae (I) and (II) can likewise be used either alone or in combination with epoxy-functional co-monomers. Especially preferred epoxy-functionalized co-monomers are the 3,4-epoxycyclohexylmethyl-3',4'-epoxycyclohexyl-carboxylate disclosed in DE-A-196 48 283 and tetrakis-(3,4-epoxy-cyclohexylethyl)-tetramethyltetracyclosiloxane.

For curing these epoxy-functionalized monomers, oligomers or polymers, cation formers according to constituent (c) are used. As cation formers it is possible to use acid formers such as Lewis or Broensted acids or compounds that release such acids, which initiate cationic polymerization, for example $BF_3$ or its ether adducts ($BF_3{}^+THF$, $BF_3{}^+Et_2O$, etc.), $AlCl_3$, $FeCl_3$, $HPF_6$, $HAsF_6$, $HSbF_6$, $HBF_4$ or substances that initiate polymerization after irradiation by UV or visible light or by heat and/or pressure, such as (eta-6-cumene)(eta-5-cyclopentadienyl)-iron- hexafluoroantimonate, substituted diaryl-iodonium salts and triarylsulphonium salts. As accelerators it is possible to use peroxy compounds such as per-esters, diacyl peroxides, peroxydicarbonates and hydroperoxides. Use of hydroperoxides is preferred, and cumene hydroperoxide in approx. 70–90% solution in cumene is especially preferred for use as an accelerator. The ratio of photo-initiator to cumene hydroperoxide can be varied over a wide range from 1:0.001 to 1:10, but preferably a ratio from 1:0.1 to 1:6 is used, and a ratio from 1:0.5 to 1:4 is especially preferred. It is also possible to use complexing agents, for example oxalic acid, 8-hydroxyquinoline, ethylenediamine-tetraacetic acid and aromatic polyhydroxy compounds. Bases, typically tertiary amines, can be added as retarders.

Suitable fillers that can be used in conjunction with the ethylenically unsaturated or the epoxy-functionalized oligomers or polymers according to unsaturated constituent (b), are inorganic fillers as a rule. Quartz, ground glasses, silica gels and pyrogenic silicas or their granules may be mentioned as examples. It is preferable for radiopaque fillers to be used as well, at least partially. These can on the one hand be radiopaque glasses, i.e. glasses containing e.g. strontium, barium or lanthanum, or part of the fillers may consist of a radiopaque additive, for example yttrium trifluoride, strontium hexafluorozirconate or fluorides of the rare-earth metals. For better incorporation in the polymer matrix it is advantageous to hydrophobize the inorganic fillers. Common hydrophobizing agents are silanes, for example trimethoxy-methacryloyloxypropylsilane, or trimethoxyglycidylsilane. The fillers preferably have a mean granulometry <20 $\mu$m and especially <5 $\mu$m and an upper limit of grain size of 150, preferably 70 $\mu$m and especially 25 $\mu$m. Mixtures of 5–25 wt. % of fillers with a mean grain size of 0.02–0.06 $\mu$m and 65–85 wt. % of fillers with a mean grain size of 1–5 $\mu$m are especially preferred.

Compounds with the general formulae (I) and (II), which set by a cement reaction, preferably contain free carboxyl groups. Polycarboxylic acids, based on acrylic acid, methacrylic acid, maleic acid, fumaric acid or itaconic acid as monomers, have for example been used until now for the so-called glass-ionomer cements. A disadvantage of cements which set with these polycarboxylic acids is that, in comparison with other dental filling materials, they display only very poor values of bending strength. One cause of this is considered to be the great flexibility of the polycarboxylic acid chains, which do not lead to sufficient stiffness of the cured material. Attempts to increase the density of carboxyl groups per monomer unit generally result in polymers that are no longer sufficiently water-soluble for use in a cement system.

Polymeric acids, which have a C—C double bond and a saturated five-membered ring in their polymer chain according to formula (I) and (II), and which are known from the literature, can be produced from 5,6-carboxyl-substituted norbornenes by ROMP. These polymeric acids have a molar weight per carbonyl group of 105–107 g/mol and surprisingly, despite their markedly lower density of carboxyl groups, compared with traditional polymeric acids, they have very good solubility in water. Furthermore, these polymeric acids obtained by ROMP set with acid-soluble glass powders, forming a cement. Moreover, these acids offer the possibility of being further modified by subsequent reactions. For example, the chain length of these molecules can be adapted to the needs of the particular application by oxidative cleavage according to the following scheme.

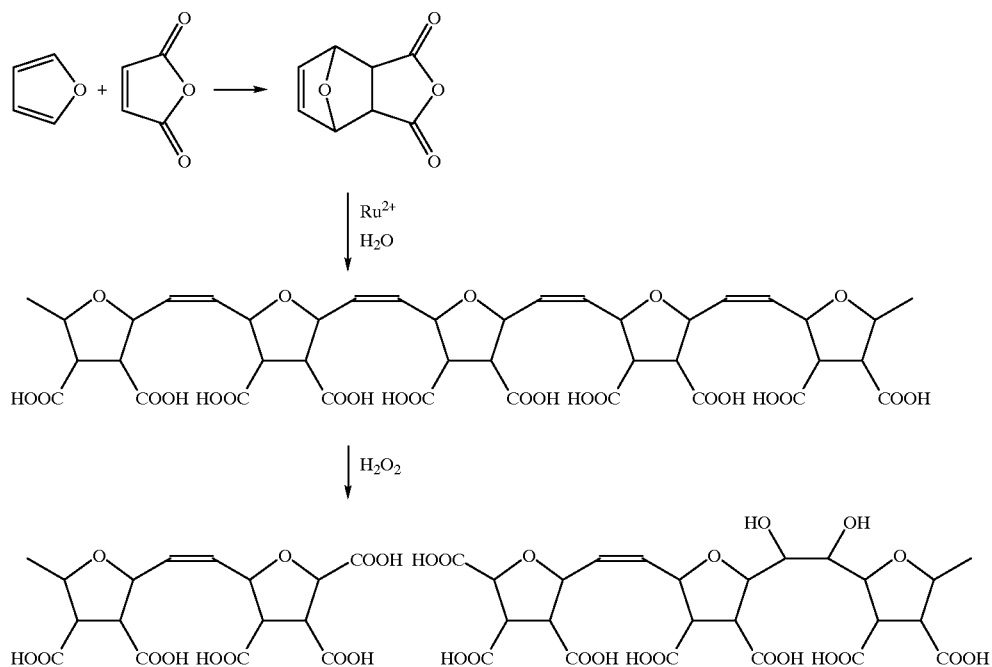
Scheme: ROMP for production of acid-functional oligomers and polymers, and their oxidative degradation.
Especially preferred compounds that can be used in cements are shown in formulae (XIV) to (XXIV) (with $m=1000$ to $3000$):
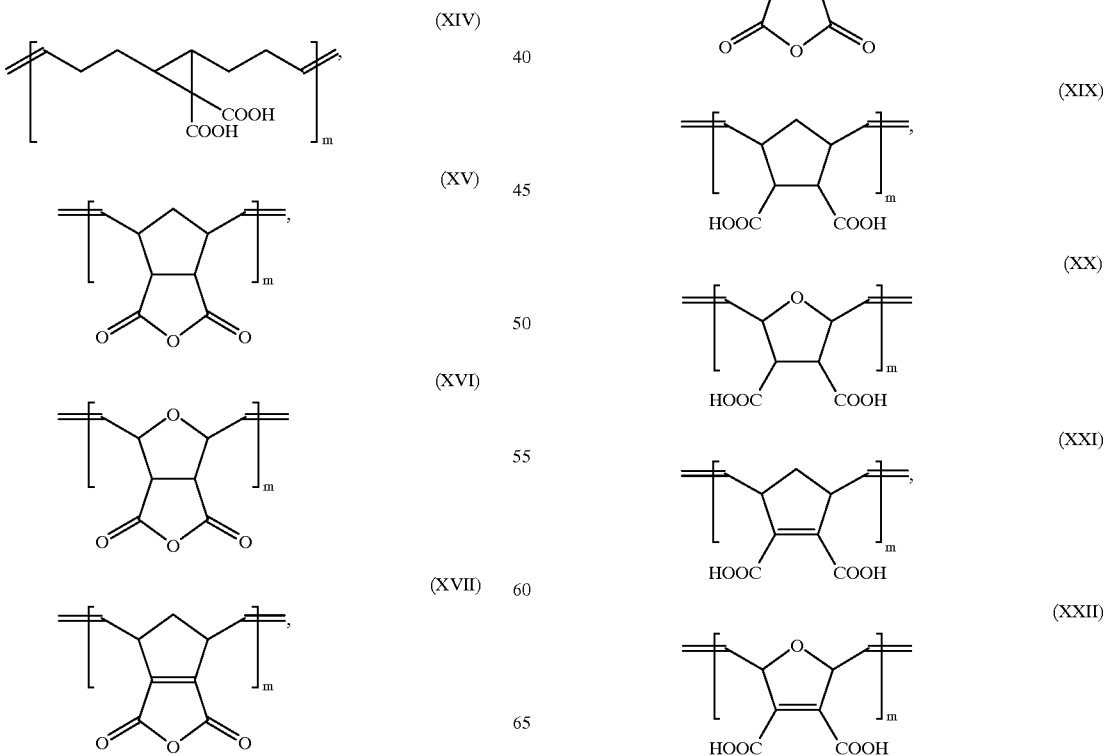

-continued

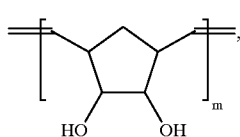

(XXIII)

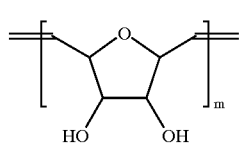

(XXIV)

Compound (XIV) can be produced according to the information from A. Demonceau et al. in Macromolecules (1997), 30, pages 3127 to 3136. Compounds (XV) to (XXIV) can once again be synthesized from the corresponding precursors as described in "Comprehensive organometallic Chemistry II: a review of the literature 1982–1994", Elsevier 1995, pages 1209–1232.

For use in dental compositions, the polymeric acids described here can either be used alone or in combination with known acids that are already used for cements. Such acids are described for example in DE-A-2 101 889.

As acid-soluble powders according to constituent (b), it is possible to use conventional silicate cement powders, as also described in DE-A-2 101 889. However, it is especially advantageous to use calcium-aluminium-fluosilicate glass powders, which are described in DE-A-2 061 513. Suitable silicate cement powders are also indicated in "Chemical Society Reviews" (1978), 7 (2), 265–296.

Dental cements are usually employed in the form of a two-component system, which consists of a liquid component and a powder component. The oligomeric and polymeric acids according to the invention can, according to one embodiment i) of the invention, be part of the mixing liquid and can, according to another embodiment ii), be part of the powder component:

In the first case mentioned (i) the mixing liquid consists of an aqueous solution of the previously defined oligomeric or polymeric acids and of conventional polymeric acids and usual additives if required. The acid-containing monomers are generally at a concentration of at least 20%, generally 30 to 60 wt. %, especially 40 to 50 wt. % in the aqueous solution, if the cement system is intended as tooth filling cement. Even lower concentrations are advantageous for fixing cements and for prosthetic purposes. The aqueous solutions should have viscosities of at least 0.5 poise, though at most 300 poise. A preferred viscosity range is between 2 and 200, especially between 5 and 100 poise (at 25° C.).

It is usual for dental cements to be sold pre-dosed in so-called shaking capsules. In these, the liquid and the powder are provided in two separate compartments, and they are combined and mixed mechanically immediately before use. This pre-dosing can also be applied to the dental compositions according to the invention.

According to the other advantageous embodiment (ii) of the invention, the mixing component of the dental cements, i.e. the oligomeric or polymeric acids according to constituent (a), is a constituent of the powder mixture and is provided as a premix of glass powder and acid-functional oligomers or polymers. The mixing component can then simply be mixed with water, with the usual additives if required.

There can be smooth transitions between the two embodiments i) and ii): for example, the oligomeric and polymeric acids can each be added as a half to the liquid and the powdered mixing component.

Also in the case of embodiment ii), it may be desirable to provide it pre-dosed in shaking capsules and market it as such. It may also be especially advantageous to compact the powder mixture as a tablet.

Apart from their use in dental cements, compounds XIV to XXIV can also be used as adherents in so-called bonding compositions. These are used either without filler (0 wt. % of component (b)) or with low filler content (5 to 30 wt. % of component (b)).

Suitable auxiliaries according to component (d) are for example the stabilizers, pigments or diluents that are usually employed in dentistry. In the case of the cement-setting systems, chelating agents, preferably tartaric acid, can be added both to the powder component and to the liquid component, to improve the curing characteristics [see DE-A-2 319 715].

The dental compositions according to the invention are suitable for the production of filling materials, fixing cements, inlays, onlays, veneer shells, temporary crown and bridge materials, dentistry materials and impression materials.

The following examples will provide a more detailed explanation of the invention.

EXAMPLES

Example 1

Synthesis and Oxidative Decomposition of Poly-7-oxabicyclo-[2.2.1]-hept-5-ene-2,3-dicarboxylic Acid 30 g exo-7-oxabicyclo[2.2.1]-hept-5-ene-2,3-dicarboxylic anhydride is heated together with a solution of $K_2[RuCl_5]*xH_2O$ in 105 g water, to 60° C., with stirring. After about 45 minutes a clear, highly viscous solution forms. This is heated to 90° C. and a total of 10.0 g of 30% hydrogen peroxide solution is added to it dropwise within one hour. Then the solution is evaporated to dryness and diluted with water to about 50%.

Example 2

Production of a Glass-ionomer Cement with Polymeric Acids According to the Invention 200 mg of the aqueous solution from Example 1 is mixed with 200 mg of an aqueous polycarboxylic acid solution (CHELON-FIL liquid, made by ESPE, Seefeld). Using a spatula, this mixture is worked to a paste with 1.2 g of reactive glass powder (CHELON-FIL Powder, made by ESPE, Seefeld). For determination of compressive and bending strength, the freshly mixed cement is placed in the appropriate test-piece moulds and left until completion of setting (approx. 5 minutes). Then the test-pieces are removed from the moulds and are tested in a Zwick Universal Tester in accordance with ISO Standard 4049 and ISO Standard 9917. The results of material testing are shown in Table 1.

Example 3

Production of a Single-component Radical-polymerizing Dental Filling Material 30 g Exo-7-oxabicyclo[2.2.1]-hept-5-ene-2,3-dicarboxylic anhydride is dissolved in 23.5 g hydroxyethylene methacrylate (HEMA) and stirred for 10 hours. Then it is taken up with a solution of 105 g water and $K_2[RuCl_5]$ *$xH_2O$ (approx. 140 mg/ml) and heated to 60° C., with stirring. After about 45 minutes, a clear, highly viscous solution forms, and this is dried at high vacuum for several hours. Then the high-viscosity residue is diluted with 10 g triethyleneglycol-dimethacrylate (TEGDMA). 10 g of this mixture is mixed with 10 g bis-(hydroxymethyl)-tricyclo [5.2.1.0$^{2,6}$]-decane-diacrylate and 0.07 g camphor-quinone, and is then kneaded to a homogeneous paste with 0.5 g highly disperse silicon dioxide (Aerosil OX50, from Degussa) and 79.5 g finely-ground quartz powder. For determination of compressive and bending strength, the paste is placed in the appropriate test-piece moulds and exposed to light in accordance with ISO Standard 4049 or ISO Standard 9917. The volume shrinkage is determined by Linometer measurement. The results of material testing are shown in Table 2.

Example 4

Production of a Single-component Cationically Polymerizing Dental Filling Material 10 g of the polymer which can be obtained by ROMP from monomer 9 in the literature citation A. Demonceau, A. W. Stumpf, E. Saive, A. F. Noels; Macromolecules (1997), 30, 3127–3136, is mixed with 10 g 3,4-epoxy-cyclohexylmethyl-3',4'-epoxycyclohexylcarboxylate, 0.8 g ferrocenium-hexafluoro-antimonate and 0.9 g cumene hydroperoxide and is then kneaded to a homogeneous paste with 0.5 g of highly disperse silicon dioxide (Aerosil OX50, from Degussa) and 79.5 g of finely-ground quartz powder. For determination of compressive and bending strength, the paste is placed in the appropriate test-piece moulds and exposed to light in accordance with ISO Standard 4049 or ISO Standard 9917. Volume shrinkage is determined by Linometer measurement. The results of material testing are shown in Table 3.

TABLE 1

Mechanical properties of the glass-ionomer cement according to the invention, in comparison with a known glass-ionomer cement

|  | Example 2 | Ketac-Fil (from ESPE, Seefeld) |
|---|---|---|
| Compressive strength [MPa]$^{a)}$ | 157 | 165 |
| Bending strength [MPa]$^{b)}$ | 52 | 35 |

TABLE 2

Mechanical properties of the dental composition according to Example 3 in comparison with a known composite filling material

|  | Example 3 | Pertac-II (from ESPE, Seefeld) |
|---|---|---|
| Compressive strength [MPa]$^{a)}$ | 412 | 420 |
| Bending strength [MPa]$^{b)}$ | 98 | 110 |
| Volume shrinkage [%]$^{c)}$ | 1.6 | 2.3 |

TABLE 3

Mechanical properties of the dental composition according to Example 4 in comparison with a known composite filling material

|  | Example 4 | Pertac-II (from ESPE, Seefeld) |
|---|---|---|
| Compressive strength [MPa]$^{a)}$ | 390 | 420 |
| Bending strength [MPa]$^{b)}$ | 90 | 110 |
| Volume shrinkage [%]$^{c)}$ | 1.4 | 2.3 |

$^{a)}$Measured according to ISO Standard 4049
$^{b)}$Measured according to ISO Standard 9917
$^{c)}$Measured with ACTA-Linometer (A. J. de Gee, A. J. Feilzer, C. L. Davidson; Dent Mat (1993), 9, 11–14)

a) Measured according to ISO Standard 4049 b) Measured according to ISO Standard 9917 c) Measured with ACTA-Linometer (A. J. de Gee, A. J. Feilzer, C. L. Davidson; Dent Mat (1993), 9, 11–14)

What is claimed is:
1. Dental composition consisting of:
   (a) 5 to 70 wt. %, relative to (a)+(b)+(d), of oligomers and/or polymers,
   (b) 0 to 95 wt. %, relative to (a)+(b)+(d), of fillers,
   (c) 0.01 to 3 wt. %, relative to (a), of at least one initiator or one initiator system,
   (d) 0 to 95 wt. %, relative to (a)+(b) +(d), of adjuncts, selected from the group consisting of pigments, radiopaque additives, thixotropy auxiliaries, stabilizers, diluents, chelating agents, and mixtures thereof, wherein 5 to 100 wt. % of component (a) comprises oligomers or polymers with the general formula

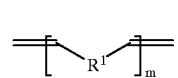 (I)

or

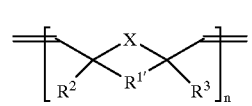 (II)

in which:
X denotes $CH_2$, NH, O or S,
m denotes a value from 10 to 20 000,
n denotes a value from 10 to 20 000,
$R^1$ denotes —$CHR^4$—$CHR^5$—, —$CR^4$—$CR^5$—,

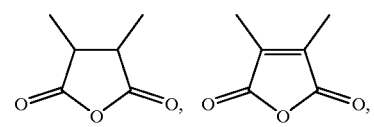

$C_2$–$C_{10}$ alkylene, $C_2$–$C_{10}$-alkenylene, $C_2$–$C_{10}$ epoxyalkylene, or $C_6$–$C_{15}$-o-arylene which can be substituted by alkyl, OH, $NH_2$, C(O)$OR^6$, C(O)$NHR^6$, $PO_3H$, $SO_3H$, Cl, Br or F,

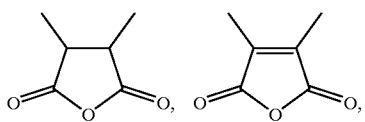

$R^{1'}$ denotes —CHR⁴—CHR⁵—, —CR⁴=CR⁵—, $R^2$, $R^3$, $R^4$, $R^5$ denote H, $C_1$–$C_{15}$ alkyl, C(O)OR⁶, C(O)NHR⁶, PO₃H, SO₃H, OH, wherein $R^4$ and $R^5$ are the same, and $R^6$ denotes H or a linear, branched or cyclic $C_1$–$C_{30}$-alkyl or -aryl residue, which can contain 0–10 O or N atoms and 0 to 5 carbonyl groups and is either saturated or unsaturated, with the proviso that these oligomers and polymers contain a group which allows curing of the composition by radical or cationic polymerization or by a cement reaction.

2. Dental composition according to claim 1, wherein said composition contains the components (a) to (d) in the following proportions:

(a) 10 to 60 wt. %, relative to (a)+(b)+(d)
(b) 40 to 85 wt. %, relative to (a)+(b)+(d)
(c) 0.05 to 2.0 wt. %, relative to (a), and
(d) 0 to 30 wt. %, relative to (a)+(b)+(d).

3. Dental composition according to claim 1, wherein component (a) can be cured by radical polymerization.

4. Dental composition according to claim 1, wherein component (a) is ethylenically unsaturated.

5. Dental composition according to claim 1, wherein component (a) contains acrylate and/or methacrylate groups.

6. Dental composition containing
(a) 5 to 70 wt. %, relative to (a)+(b)+(d), of oligomers and/or polymers,
(b) 0 to 95 wt. %, relative to (a)+(b)+(d), of fillers,
(c) 0.01 to 3 wt. %, relative to (a), of at least one initiator or one initiator system,
(d) 0 to 95 wt. %, relative to (a)+(b)+(d), of adjuncts, selected from the group consisting of pigments, radiopaque additives, thixotropy auxiliaries, stabilizers, diluents, chelating agents, and mixtures thereof, wherein 5 to 100 wt. % of component (a) comprises oligomers or polymers with the general formula

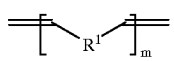  (I)

or

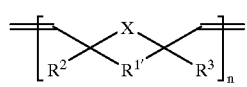  (II)

in which:
X denotes CH₂, NH, O or S,
m denotes a value from 10 to 20 000,
n denotes a value from 10 to 20 000,
$R^1$ denotes —CHR⁴—CHR⁵—, —CR⁴—CR⁵—,

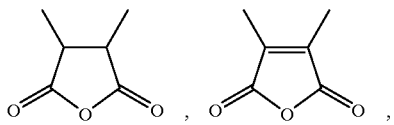

$C_2$–$C_{10}$ alkylene, $C_2$–$C_{10}$-alkenylene, $C_2$–$C_{10}$ epoxyalkylene, or $C_6$–$C_{15}$-o-arylene which can be substituted by alkyl, OH, NH₂, C(O)OR⁶, C(O)NHR⁶, PO₃H, SO₃H, Cl, Br or F, $R^{1'}$ denotes —CHR⁴—CHR⁵—, —CR⁴=CR⁵—,

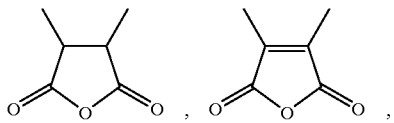

$R^2$, $R^3$, $R^4$, $R^5$ denote H, $C_1$–$C_{15}$ alkyl, C(O)OR⁶, C(O)NHR⁶, PO₃H, SO₃H, OH, wherein $R^4$ and $R^5$ are the same, and $R^6$ denotes H or a linear, branched or cyclic $C_1$–$C_{30}$-alkyl or -aryl residue, which can contain 0–10 O or N atoms and 0 to 5 carbonyl groups and is either saturated or unsaturated, wherein component (a) can be cured by cationic polymerization.

7. Dental composition according to claim 6, wherein component (a) contains epoxy groups.

8. Dental composition according to claim 1, wherein component (a) can be cured by a cement reaction.

9. Dental composition according to claim 8, wherein said composition is a powder component and a mixing liquid, and component (a) is contained in the powder component.

10. Dental composition according to claim 8, wherein said composition is a powder component and a mixing liquid, and component (a) is contained in the mixing liquid.

11. A method for the production of a product selected from the group consisting of filling materials, fixing cements, inlays, onlays, veneer shells, temporary crown and bridge materials, pattern materials, and impression materials, which comprises forming the product by using the dental composition according to claim 1.

12. Dental composition according to claim 6, wherein component (a) is a compound of formula (XIV)

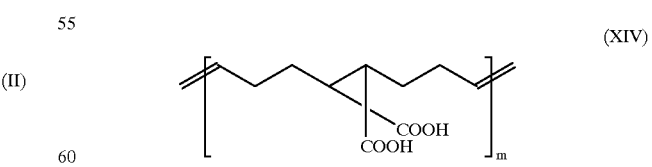  (XIV)

wherein m is 1000 to 3000.

13. Dental composition according to claim 1, wherein component (a) is a compound of formula (XV)

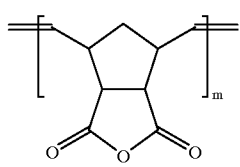

(XV)

wherein m is 1000 to 3000.

14. Dental composition according to claim 1, wherein component (a) is a compound of formula (XVI)

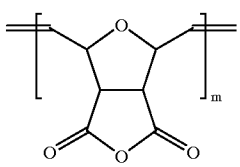

(XVI)

wherein m is 1000 to 3000.

15. Dental composition according to claim 6, wherein component (a) is a compound of formula (XVII)

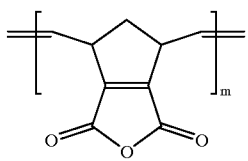

(XVII)

wherein m is 1000 to 3000.

16. Dental composition according to claim 6, wherein component (a) is a compound of formula (XVIII)

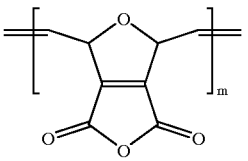

(XVIII)

wherein m is 1000 to 3000.

17. Dental composition according to claim 1, wherein component (a) is a compound of formula (XIX)

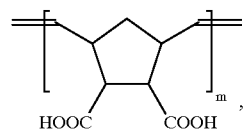

(XIX)

wherein m is 1000 to 3000.

18. Dental composition according to claim 1, wherein component (a) is a compound of formula (XX)

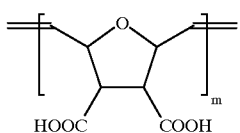

(XX)

wherein m is 1000 to 3000.

19. Dental composition according to claim 6, wherein component (a) is a compound of formula (XXI)

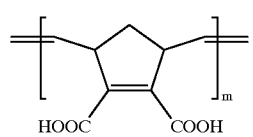

(XXI)

wherein m is 1000 to 3000.

20. Dental composition according to claim 6, wherein component (a) is a compound of formula (XXII)

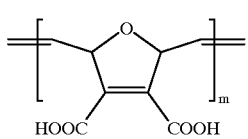

(XXII)

wherein m is 1000 to 3000.

21. Dental composition according to claim 6, wherein component (a) is a compound of formula (XXIII)

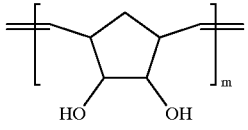

(XXIII)

wherein m is 1000 to 3000.

22. Dental composition according to claim 6, wherein component (a) is a compound of formula (XXIV)

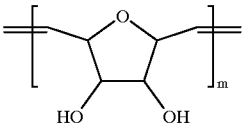

(XXIV)

wherein m is 1000 to 3000.

23. Dental composition according to claim 1, wherein the oligomers and polymers of component (a) are obtained by ring-opening metathesis polymerization.

* * * * *